US010118955B2

(12) United States Patent
Habener et al.

(10) Patent No.: US 10,118,955 B2
(45) Date of Patent: *Nov. 6, 2018

(54) C-TERMINAL FRAGMENTS OF GLUCAGON-LIKE PEPTIDE-1 (GLP-1)

(71) Applicant: The General Hospital Corporation, Boston, MA (US)

(72) Inventors: Joel F. Habener, Newton Center, MA (US); Tatsuya Yano, Tokyo (JP); Eva Tomas Falco, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/539,578

(22) Filed: Nov. 12, 2014

(65) Prior Publication Data

US 2015/0133384 A1    May 14, 2015

Related U.S. Application Data

(62) Division of application No. 13/127,387, filed as application No. PCT/US2009/063746 on Nov. 9, 2009, now Pat. No. 8,889,618.

(60) Provisional application No. 61/181,849, filed on May 28, 2009, provisional application No. 61/175,543, filed on May 5, 2009, provisional application No. 61/112,341, filed on Nov. 7, 2008.

(51) Int. Cl.
A61K 38/26    (2006.01)
A61P 3/10    (2006.01)
A61P 7/12    (2006.01)
C07K 14/605    (2006.01)
C07K 14/005    (2006.01)
C12N 7/00    (2006.01)
A61K 38/00    (2006.01)

(52) U.S. Cl.
CPC .......... C07K 14/605 (2013.01); C07K 14/005 (2013.01); C12N 7/00 (2013.01); *A61K 38/00* (2013.01); *C07K 2319/10* (2013.01); *C12N 2740/16033* (2013.01)

(58) Field of Classification Search
CPC .............................. A61K 38/26; C07K 14/605
See application file for complete search history.

(56) References Cited

U.S. PATENT DOCUMENTS

| 5,574,008 | A | 11/1996 | Johnson et al. |
| 5,846,937 | A | 12/1998 | Drucker |
| 6,268,343 | B1 | 7/2001 | Knudsen et al. |
| 6,344,180 | B1 | 2/2002 | Holst et al. |
| 6,395,767 | B2 | 5/2002 | Robl et al. |
| 6,444,788 | B1 | 9/2002 | Staby |
| 6,458,924 | B2 | 10/2002 | Knudsen et al. |
| 6,468,798 | B1 | 10/2002 | Debs et al. |
| 6,528,486 | B1 | 3/2003 | Larsen et al. |
| 6,573,287 | B2 | 6/2003 | Sulsky et al. |
| 6,841,535 | B2 | 1/2005 | Divita et al. |
| 7,141,547 | B2 | 11/2006 | Rosen et al. |
| 9,040,481 | B2 * | 5/2015 | Habener ............... A61K 38/08 514/11.7 |
| 2001/0011071 | A1 | 8/2001 | Knudsen et al. |
| 2001/0047084 | A1 | 11/2001 | Knudsen et al. |
| 2002/0006899 | A1 | 1/2002 | Pospisilik et al. |
| 2002/0019411 | A1 | 2/2002 | Robl et al. |
| 2002/0110560 | A1 | 8/2002 | Demuth et al. |
| 2002/0183367 | A1 | 12/2002 | Sulsky et al. |
| 2003/0004095 | A1 | 1/2003 | Reimer et al. |
| 2003/0073626 | A1 | 4/2003 | Hathaway et al. |
| 2003/0091507 | A1 | 5/2003 | Holst et al. |
| 2003/0176357 | A1 | 9/2003 | Pospisilik et al. |
| 2003/0199451 | A1 | 10/2003 | Mogensen et al. |
| 2003/0199672 | A1 | 10/2003 | Knudsen et al. |
| 2003/0220243 | A1 | 11/2003 | Glaesner et al. |
| 2003/0220274 | A1 | 11/2003 | Oh et al. |
| 2003/0225102 | A1 | 12/2003 | Sankaranarayanan |
| 2004/0266678 | A1 | 12/2004 | Beeley et al. |
| 2006/0014241 | A1 | 1/2006 | Glaesner et al. |
| 2006/0183682 | A1 | 8/2006 | Juul-Mortensen |
| 2008/0194483 | A1 | 8/2008 | Brownlee |
| 2008/0300173 | A1 | 12/2008 | Defrees |
| 2009/0030178 | A1 * | 1/2009 | Chang .................. C07K 14/005 530/324 |
| 2009/0136585 | A1 | 5/2009 | Labhasetwar et al. |
| 2009/0227519 | A1 | 9/2009 | Balasubramaniam |
| 2009/0292108 | A1 * | 11/2009 | Chen .................... C07K 14/605 530/326 |
| 2010/0184645 | A1 | 7/2010 | Verdine et al. |

(Continued)

FOREIGN PATENT DOCUMENTS

EP    0708179 A2    10/1995
EP    0699686 A2    3/1996

(Continued)

OTHER PUBLICATIONS

Knudsen et al. "Potent Derivatives of Glucagon-like Peptide-1 with Pharmacokinetic Properties Suitable for Once Daily Administration" J. Med. Chem. 43:1664-1669. Published 2000.*

(Continued)

Primary Examiner — Christina Bradley
Assistant Examiner — Zachary J Miknis
(74) Attorney, Agent, or Firm — Fish & Richardson P.C.

(57) ABSTRACT

C-Terminal Fragments of Glucagon-Like Peptide-1 (GLP 1), and methods of use thereof, e.g., for the treatment of obesity and obesity-related disorders, e.g., diabetes and the metabolic syndrome.

18 Claims, 6 Drawing Sheets
Specification includes a Sequence Listing.

(56) References Cited

U.S. PATENT DOCUMENTS

| | | |
|---|---|---|
| 2010/0286024 A1 | 11/2010 | Kanda |
| 2013/0288961 A1 | 10/2013 | Habener et al. |
| 2014/0212472 A1 | 7/2014 | Habener et al. |

FOREIGN PATENT DOCUMENTS

| | | | |
|---|---|---|---|
| EP | | 1076066 | 2/2001 |
| EP | | 1196444 B1 | 6/2003 |
| EP | | 1329458 A2 | 7/2003 |
| EP | | 0708179 B1 | 12/2004 |
| WO | WO 1991/011457 | | 8/1991 |
| WO | WO 1996/006628 | | 3/1996 |
| WO | WO 1998/008871 | | 3/1998 |
| WO | WO 1998/039022 | | 9/1998 |
| WO | WO 1999/038501 | | 8/1999 |
| WO | WO 1999/043705 | | 9/1999 |
| WO | WO 1999/043706 | | 9/1999 |
| WO | WO 1999/043708 | | 9/1999 |
| WO | WO 1999/053064 | | 10/1999 |
| WO | WO 2000/077039 | | 12/2000 |
| WO | WO 2001/037850 | | 5/2001 |
| WO | WO 2001/068603 | | 9/2001 |
| WO | WO 2001/098331 | | 12/2001 |
| WO | WO 2002/047716 | | 6/2002 |
| WO | WO 2002/062764 | | 8/2002 |
| WO | WO 2002/083128 | | 10/2002 |
| WO | WO 2002/085406 | | 10/2002 |
| WO | WO 2003/018516 | | 3/2003 |
| WO | WO 2003/028626 | | 4/2003 |
| WO | WO 2003/038123 | | 5/2003 |
| WO | WO 2003/045977 | | 6/2003 |
| WO | WO 2003/061362 | | 7/2003 |
| WO | WO 2003/072195 | | 9/2003 |
| WO | WO 2003/099991 | | 12/2003 |
| WO | WO 2003/103572 | | 12/2003 |
| WO | WO 2005/060986 | | 7/2005 |
| WO | 2007/024899 | | 3/2007 |
| WO | 2007/030706 | | 3/2007 |
| WO | WO 2007/051987 | | 5/2007 |
| WO | WO2007051987 A1 * | | 5/2007 |
| WO | WO2007061434 A2 * | | 5/2007 |
| WO | WO 2007/065156 | | 6/2007 |
| WO | WO 2009/051259 | | 4/2009 |
| WO | WO 2010/054326 | | 5/2010 |
| WO | WO 2010/093802 | | 8/2010 |
| WO | 2012/061466 | | 5/2012 |

OTHER PUBLICATIONS

Green et al. "Degradation, receptor binding, insulin secreting and antihyperglycaemic actions of palmitate-derivatised native and Ala8-substituted GLP-1 analogues" Biol. Chem. 385:169-177. Published Feb. 2004.*
Sato et al. "Therapeutic peptides: technological advances driving peptides into development" Curr. Opin. Biotech. 17:638-642. Published online Oct. 17, 2006.*
Hupe-Sodmann et al. "Characterisation of the processing by human neutral endopeptidase 24.11 of GLP-1(7-36)amide and comparison of the substrate specificity of the enzyme for other glucagon-like peptides" Regulatory Peptides 58:149-156, published 1995.*
Abu-Hamdah et al., "Clinical review: The extrapancreatic effects of glucagon-like peptide-1 and related peptides," J. Clin. Endocrinol. Metab., 94:1843-1852, Jun. 2009.
Authier et al., "Endosomal Proteolysis of Glucagon at Neutral pH Generates the Bioactive Degradation Product Miniglucagon-(19-29)," Endocrinology, 144(12):5353-5364, Dec. 2003.
Ban et al., "Cardioprotective and vasodilatory actions of glucagon-like peptide 1 receptor are mediated through both glucagon-like peptide 1 receptor-dependent and -independent pathways," Circulation, 117(18):2340-2350, Apr. 2008.
Ban et al., "Glucagon-like peptide (GLP)-1(9-36)amide-mediated cytoprotection is blocked by exendin (9-39) yet does not require the known GLP-1 receptor," Endocrinology, 151:1520-1531, February.

Bebernitz et al., "The Impact of Fatty Acid Oxidation on Energy Utilization: Targets and Therapy," Current Pharmaceutical Design, 8:1199-1227, Jun. 2002.
Brun et al., "Intracellular targeting of truncated secretory peptides in the mammalian heart and brain," FASEB J., 20:732-734, Jan. 2006.
Communication issued in EP 09825560.7 dated Apr. 15, 2014, 8 pages.
Dalle et al., "Miniglucagon (Glucagon 19-29) A Novel Regulator of the Pancreatic Islet Physiology," Diabetes, 51:406-412, Feb. 2002.
Dayhoff et al., "Establishing homologies in protein sequences," Methods Enzymol., 91:524-545, Jan. 1983.
De Meester et al., "CD26, let it cut or cut it down," Immunol Today, 20:367-375, Aug. 1999.
Deacon, "Circulation and degradation of GIP and GLP-1," Horm. Metab. Res., 36:761-5, Nov. 2004.
Ding et al., "Exendin-4, a Glucagon-Like Protein-1 (GLP-1) Receptor Agonist, Reverses Hepatic Steatosis in ob/ob Mice," Hepatology, 43:173-181, Jan. 2006.
Dobrzyn et al., "Stearoyl-CoA desaturase 1 deficiency increases fatty acid oxidation by activating AMP-activated protein kinase in liver," Proc. Natl. Acad. Sci. USA, 101(17):6409-6414, Apr. 2004.
Drucker, "The biology of incretin hormones," Cell. Metab., 3:153-165, Mar. 2006.
Egan et al., "Glucagon-Like Peptide-1 Augments Insulin-Mediated Glucose Uptake in the Obese State," The Journal of Clinical Endocrinology & Metabolism, 87(8)3768-3773, Aug. 2002.
Elahi et al., "GLP-1 (9-36) amide, cleavage product of GLP-1 (7-36) amide, is a glucoregulatory peptide," Obesity (Silver Spring), 16(7):1501-1509, Jul. 2008.
Elahi et al., "The Insulinomimetic Actions of GLP-1(9-36) Amide, Cleavage Product of GLP-1(7-36) Amide," Diabetes, 55(Suppl 1):A85 (Abstract 363-OR), 2006.
Farooqui et al., "Metabolic syndrome as a risk factor for neurological disorders," Cell. Mol. Life. Sci., 69:741-762, Oct. 2011.
Ferrand et al., "Involvement of JAK2 upstream of the PI 3-kinase in cell-cell adhesion regulation by gastrin," Exp. Cell. Res., 301:128-138, Dec. 2004.
Flock et al., "Incretin receptors for glucagon-like peptide 1 and glucose-dependent insulinotropic polypeptide are essential for the sustained metabolic actions of vildagliptin in mice," Diabetes, 56:3006-13, Dec. 2007.
Grattagliano et al., "Oxidative stress-induced risk factors associated with the metabolic syndrome: a unifying hypothesis," J. Nutr. Biochem., 19:491-504, Aug. 2008.
Green et al., "GLP-1 and related peptides cause concentration-dependent relaxation of rat aorta through a pathway involving KATP and CAMP," Arch. Biochem. Biophys., 478:136-142, Aug. 2008.
Haas et al., "Dissecting the Role of Insulin Resistance in the Metabolic Syndrome," Curr. Opin. Lipidol., 20:206-210, Jun. 2009.
Hansen et al., "Glucagon-like peptide-1-(7-36)amide is transformed to glucagon-like peptide-1-(9-36)amide by dipeptidyl peptidase IV in the capillaries supplying the L cells of the porcine intestine," Endocrinology, 140:5356-63, Nov. 1999.
Hashimoto et al., "A new inhibitor of mitochondrial fatty acid oxidation," J. Biochem., 119(6):1196-1201, Jun. 1996.
Hirst, "Towards the molecular mechanism of respiratory complex I," J. Biochem., 425:327-339, Dec. 2009.
Hupe-Sodmann et al., "Characterisation of the processing by human neutral endopeptidase 24.11 of GLP-1(7-36) amide and comparison of the substrate specificity of the enzyme for other glucagon-like peptides," Regul. Pept., 58(3):149-156, Aug. 1995.
Ibdah et al., "Lack of mitochondrial trifunctional protein in mice causes neonatal hypoglycemia and sudden death," J. Clin. Invest., 107:1403-1409, 2001.
Ibdah et al., "Mice Heterozygous for a Defect in Mitochondrial Trifunctional Protein Develop Hepatic Steatosis and Insulin Resistance," Gastroenterology, 128:1381-1390, May 2005.
International Preliminary Report on Patentability in International Application No. PCT/US2011/058907, dated May 7, 2013, 5 pages.
International Preliminary Report on Patentability in International Application No. PCT/US2012/045537, dated Jan. 16, 2014, 8 pages.

(56) References Cited

OTHER PUBLICATIONS

International Search Report and Written Opinion in International Application No. PCT/US2012/045537, dated Jan. 29, 2013, 16 pages.
International Search Report in International Application No. PCT/US2011/058907, dated May 25, 2012, 3 pages.
International Search Report issued in PCT/US2009/063746 dated Jun. 29, 2010, 15 pages.
Kieffer and Habener, "The glucagon-like peptides," Endocr. Rev., 20:876-913, Dec. 1999.
Knudsen et al., "Glucagon-like peptide-1-(9-36) amide is a major metabolite of glucagon-like peptide-1-(7-36) amide after in vivo administration of dogs, and it acts as an antagonist on the pancreatic receptor," European Journal of Pharmacology, 318:429-435, Dec. 1996.
Knudsen et al., "Potent derivatives of glucagon-like peptide-1 with pharmacokinetic properties suitable for once daily administration," J. Med. Chem., 43:1664-1669, May 2000.
Koonen et al., "Increased hepatic CD36 expression contributes to dyslipidemia associated with diet-induced obesity," Diabetes, 56:2863-2871, Dec. 2007.
Lambeir et al., "Dipeptidyl-peptidase IV from bench to bedside: an update on structural properties, functions, and clinical aspects of the enzyme DPP IV," Crit. Rev. Clin. Lab. Sci., 40:209-294, Jun. 2003.
Larter et al., "MCD-induced steatohepatitis is associated with hepatic adiponectin resistance and adipogenic transformation of hepatocytes," J Hepatol., 49:407-416, Sep. 2008.
Li et al., "GLP-1 C-terminal structures affect its blood glucose lowering function," Journal of Peptide Science, 14:777-785, Jul. 2008.
Liu et al., "Prolonged treatment of primary hepatocytes with oleate induces insulin resistance through p38 mitogen-activated protein kinase," J. Biol. Chem., 282:14205-14212, May 2007.
Lovshin and Drucker, "Incretin-based therapies for type 2 diabetes mellitus," Nat. Rev. Endocrinol., 5:262-9, May 2009.
Luchsinger, "Diabetes, related conditions, and dementia," J Neurol Sci., 299:35-38, Dec. 2010.
Meier et al., "The glucogon-like peptide-1 metabolite GLP-1(9-36)amide reduces postprandial glycemia independently of gastric emptying and insulin secretion in humans," Am. J. Physiol. Endocrinol. Metab., 290:E1118-E1123, Jun. 2006.
Meneilly et al., "Effects of 3 Months of Continuous Subcutaneous Administration of Glucagon-Like Peptide 1 in Elderly Patients with Type 2 Diabetes," Diabetes Care, 26(10):2835-2841, Oct. 2003.
Murphy et al., "Gastrin and gastrin receptor antagonists bind to both N- and C-terminal halves of the 78 kDa gastrin-binding protein," Int. J. Biochem. Cell. Biol., 28:1233-1240, Nov. 1996.
Nikolaidis et al., "Active metabolite of GLP-1 mediates myocardial glucose uptake and improves left ventricular performance in conscious dogs with dilated cardiomyopathy," Am. J. Physiol. Heart Circ. Physiol., 289:H2401-2408, Dec. 2005.
Ott et al., "Mitochondria, oxidative stress and cell death," Apoptosis, 12:913-922, May 2007.
Panza et al., "Metabolic Syndrome and Cognitive Impairment: Current Epidemiology and Possible Underlying Mechanisms," J. Alzheimers Dis., 21:691-724, Jun. 2010.
Parekh et al., "Reversal of diet-induced obesity and diabetes in C57BL/6J mice," Metabolism, 47:1089-1096, Sep. 1998.
Plamboeck et al., "Neutral endopeptidase 24.11 and dipeptidyl peptidase IV are both involved in regulating the metabolic stability of glucagon-like peptide-1 in vivo," Adv Exp Med Biol., 524:303-12, 2003.
Plamboeck et al., "Neutral endopeptidase 24.11 and dipeptidyl peptidase IV are both mediators of the degradation of glucagon-like peptide 1 in the anaesthetized pig," Diabetologia, 48(9):1882-1890, Jul. 2005.
Randle, "Regulatory interactions between lipids and carbohydrates: the glucose fatty acid cycle after 35 years," Diabetes Metab. Rev., 14:263-283, Dec. 1998.
Rodrigue-Way et al., "A growth hormone-releasing peptide promotes mitochondrial biogenesis and a fat burning-like phenotype through scavenger receptor CD36 in white adipocytes," Endocrinology, 148(3):1009-1018, Mar. 2007.
Roques et al., "Neutral endopeptidase 24.11: structure, inhibition, and experimental and clinical pharmacology," Pharmacol. Rev., 45:87-146, Mar. 1993.
Ryan et al., "Insulinotropic Hormone Glucagon-Like Peptide-1-(7-37) Appears Not to Augment Insulin-Mediated Glucose Uptake in Young Men during Euglycemia," Journal of Clinical Endocrinology and Metabolism, 83(7):2399-2404, 1998.
Sato et al., "Therapeutic peptides: technological advances driving peptides into development," Current Opinion in Biotechnology, 17(6):638-642, Dec. 2006.
She et al., "Adipogenic Transcriptional Regulation of Hepatic Stellate Cells," J, Biol, Chem,, 280:4959-4967, Feb. 2005.
Simonsen et al., "Inhibition of neutral endopeptidase 24.11 does not potentiate the improvement in glycemic control obtained with dipeptidyl peptidase-4 inhibition in diabetic Goto-Kakizaki rats," Horm. Metab. Res., 41:851-3, Nov. 2009.
Sonne et al., "Protective effects of GLP-1 analogues exendin-4 and GLP-1(9-36) amide against ischemia-reperfusion injury in rat heart," Regul. Pept., 146:243-249, Feb. 2008.
Standeven et al., "Neprilysin, obesity and the metabolic syndrome," Int J Obes (Lond), 1-10 November November 2010.
Stein et al., "Insulin sensitizers in nonalcoholic fatty liver disease and steatohepatitis," Current Status Advanced Ther., 26:893-907, Oct. 2009.
Supplementary European Search Report issued in EP09825560 dated Feb. 7, 2012.
Todd et al., "Glucagon-like peptide-1 (GLP-1): a trial of treatment in non-insulin-dependent diabetes mellitus," European Journal of Clinical Investigation, 27:533-536, Jun. 1997.
Tomas and Habener, "Insulin-like actions of glucagon-like peptide-1: A dual receptor hypothesis," Trends Endocrinol. Metab., 21:59-67, Feb. 2010.
Tomas et al., "GLP-1(9-36)amide metabolite suppression of glucose production in isolated mouse hepatocytes," Horm. Metab. Res., 42:657-662, Aug. 2010.
Tomas et al., "GLP-1-derived nonapeptide GLP-1(28-36) amide inhibits weight gain and attenuates diabetes and hepatic steatosis in diet-induced obese mice," Regulatory Peptides, 169(1-3):43-48, May 2011.
Tomas et al., "GLP-1-derived nonapeptide GLP-1(28-36) amide targets to mitochondria and suppresses glucose production and oxidative stress in isolated mouse hepatocytes," Regulatory Peptides, 167(2-3):177-184, Jan. 2011.
Tomas et al., "Glucagon-like peptide-1(9-36)amide metabolite inhibits weight gain and attenuates diabetes and hepatic steatosis in diet-induced obese mice," Diabetes Obes Metab., 13:26-33, Jan. 2011.
Tsukamoto et al., "Fat paradox of steatohepatitis," J Gastroenterol Hepatol., 23 Suppl 1:S104-107, Mar. 2008.
Unger et al., "Lipid homeostasis, lipotoxicity and the metabolic syndrome," Biochimica et Biophysica Acta., 1801:209-214, Nov. 2010.
Wanders et al., "Disorders of mitochondrial fatty acyl-CoA β-oxidation," J. Inher. Metab. Dis., 22:442-487, Jun. 1999.
Zander et al., "Effect of 6-week course of glucagon-like peptide 1 on glycaemic control, insulin sensitivity, and betta-cell function in type 2 diabetes: a parallel-group study," The Lancet, 359:824-830, Mar. 2002.
Zhang et al., "Continuous stimulation of human glucagon-like peptide-1 (7-36) amide in a mouse model (NOD) delays onset of autoimmune type 1 diabetes," Diabetologia, 50:1900-1999, Jul. 2007.
Zhao et al., "Cell-permeable Peptide Antioxidants Targeted to Inner Mitochondrial Membrane inhibit Mitochondrial Swelling, Oxidative Cell Death, and Reperfusion Injury," J. Biol. Chem., 279:34682-90, Jul. 2004.
Bonny et al., "Cell-Permeable Peptide Inhibitors of JNK Novel Blockers of β-Cell Death," Diabetes, Jan. 2001, 50:77-82.

(56) References Cited

OTHER PUBLICATIONS

Carlson et al., "Regulation of the C/EBP-related gene gadd153 by glucose deprivation," Mol. Cell Biol., Aug. 1993, 13(8):4736-44.
Caron et al., "Intracellular Delivery of a Tat-eGFP Fusion Protein into Muscle Cells," Mol. Ther., Mar. 2001, 3(3):310-8.
Deacon, "Perspectives in Diabetes, Therapeutic Strategies Based on Glucagon-Like Peptide 1," Diabetes, Sep. 2004, 53:2181-2189.
European Office Action issued in EP09825560.7 dated Feb. 29, 2012 (8 pages).
European Office Action issued in EP09825560.7 dated Apr. 15, 2014 (8 pages).
European Office Action issued in EP09825560.7 dated Oct. 8, 2015 (6 pages).
European Search Report issued in EP09825560.7 dated Feb. 15, 2012 (8 pages).
European Search Report issued in EP12807290 dated Dec. 19, 2014 (10 pages).
Fodor et al., "Recommendations for the management and treatment of dyslipidemia," Can. Med. Assoc. J., 2000, 162:1441-7.
Furuse et al. "Effects of various N-terminal fragments of glucagon-like peptide-1 (7-36) on food intake in the neonatal chick," Brain Research, 1998, 807:214-217.
International Preliminary Report on Patentability in International Application No. PCT/US2009/063746, dated May 19, 2011, 8 pages.
Lee et al., "Efficient intracellular delivery of functional proteins using cationic polymer core/shell nanoparticles," Biomaterials, 2008, 29(9):1224-1232.
Mayo et al., "Design of a Partial Peptide Mimetic of Anginex with Antiangiogenic and Anticancer Activity," J. Biol. Chem., Aug. 2003, 278:45746.
Mojsov, "Structural requirements for biological activity of glucagon-like peptide-I," Int. J. Peptide Protein Res., 1992, 40:333-343.
Mu et al., "Chronic Inhibition of Dipeptidyl Peptidase-4 With a Sitagliptin Analog Preserves Pancreatic B-Cell Mass and Function in a Rodent Model of Type 2 Diabetes," Diabetes, Jun. 2006, 55:1695-1704.
Oltman et al., "Role of the effect of inhibition of neutral endopeptidase on vascular and neural complications in streptozotocin-induced diabetic rats," Eur. J. Pharmacol., Jan. 2011, 650(2-3):556-562.
Pathak et al., "Dipeptidyl Peptidase-4 (DPP-4) Inhibitors in the Management of Diabetes," Drug Class Review, Sep. 2010, 35(9):509-513.
Suzuki et al., "Comparison of the Effects of Various C-Terminal and N-Terminal Fragment Peptides of Glucagon-Like Peptide-1 on Insulin and Glucagon Release from the Isolated Perfused Rat Pancreas," Endocrinology, 1989, 125(6):3109-3114.
Szeto, "Cell-permeable, Mitochondrial-targeted, Peptide Antioxidants," AAPS Journal 2006; 8(2) Article 32, 7 pages.
Tomas et al., "Abstract 1915-P:GLP-1-Derived Pentapeptide GLP-1(32-36)amide Attenuates the Development of Obesity, Diabetes, Heaptic Steatosis and Increases Energy Expenditure in Diet-Induced Obese Mice," 72nd Scientific Sessions, American Diabetes Association, (Jun. 2012) Retrieved from the Internet: URL:http://www.abstractsonline.com/Plan/AbstractPrintView.aspx?mID=2936&sKey=b266eaf6-c060-450a-9a54-ae244aae03af&cKey=e1f51b44-b39f-49dc-b2bd-44c011d595ea [retrieved on Dec. 18, 2014].
U.S. Final Office Action in U.S. Appl. No. 13/127,387, dated Jan. 14, 2014, 13 pages.
U.S. Final Office Action in U.S. Appl. No. 14/128,801, dated Jun. 29, 2015, 11 pages.
U.S. Non-Final Office Action in U.S. Appl. No. 13/127,387, dated Sep. 19, 2013, 17 pages.
U.S. Non-Final Office Action in U.S. Appl. No. 13/882,825, dated May 28, 2014, 34 pages.
U.S. Non-Final Office Action in U.S. Appl. No. 14/128,801, dated Jan. 5, 2015, 18 pages.
U.S. Non-Final Office Action in U.S. Appl. No. 14/128,801, dated Feb. 19, 2016, 13 pages.
U.S. Notice of Allowance in U.S. Appl. No. 13/127,387, dated Jul. 21, 2014, 14 pages.
U.S. Notice of Allowance in U.S. Appl. No. 13/882,825, dated Jan. 30, 2015, 17 pages.
Vahl et al., "Effects of GLP-1-(7-36)NH2, GLP-1-(7-37), and GLP-1-(9-36)NH2 on Intravenous Glucose Tolerance and Glucose-Induced Insulin Secretion in Healthy Humans," The Journal of Clinical Endocrinology &.Metabolism, Apr. 2003, 88(4):1772-1779.
Xiong et al., "New insight into the mechanisms underlying the function of the incretin hormone glucagon-like peptide-1 in pancreatic β-cells," Landes Bioscience, 2012, 4(6):359-365.
European Office Action issued in EP12807290.7 dated Jun. 14, 2016 (7 pages).
European Office Action in Application No. 12807290.7, dated Jun. 16, 2017, 6 pages.

\* cited by examiner

SEQUENCE LISTING

```
<160> NUMBER OF SEQ ID NOS: 32

<210> SEQ ID NO 1
<211> LENGTH: 12
<212> TYPE: PRT
<213> ORGANISM: Artificial Sequence
<220> FEATURE:
<223> OTHER INFORMATION: peptide fragments
<220> FEATURE:
<221> NAME/KEY: VARIANT
<222> LOCATION: 12
<223> OTHER INFORMATION: Xaa = Any Amino Acid

<400> SEQUENCE: 1

Phe Tyr Ile Ala Trp Leu Val Lys Arg Gly Arg Xaa
1               5                   10

<210> SEQ ID NO 2
<211> LENGTH: 3
<212> TYPE: PRT
<213> ORGANISM: Artificial Sequence
<220> FEATURE:
<223> OTHER INFORMATION: peptide fragments

<400> SEQUENCE: 2

Gly Leu Pro
1

<210> SEQ ID NO 3
<211> LENGTH: 12
<212> TYPE: PRT
<213> ORGANISM: Artificial Sequence
```

```
<220> FEATURE:
<223> OTHER INFORMATION: peptide fragments

<400> SEQUENCE: 3

Ala Lys Glu Phe Ile Ala Trp Leu Val Lys Gly Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: peptide fragments

<400> SEQUENCE: 4

Ala Lys Glu Phe Ile Ala Trp Leu Val Lys
1               5                   10

<210> SEQ ID NO 5
<211> LENGTH: 9
<212> TYPE: PRT
<213> ORGANISM: Artificial Sequence
<220> FEATURE:
<223> OTHER INFORMATION: peptide fragments

<400> SEQUENCE: 5

Phe Ile Ala Trp Leu Val Lys Gly Arg
1               5

<210> SEQ ID NO 6
<211> LENGTH: 7
<212> TYPE: PRT
<213> ORGANISM: Artificial Sequence
<220> FEATURE:
<223> OTHER INFORMATION: peptide fragments

<400> SEQUENCE: 6

Phe Ile Ala Trp Leu Val Lys
1               5

<210> SEQ ID NO 7
<211> LENGTH: 10
<212> TYPE: PRT
<213> ORGANISM: Artificial Sequence
<220> FEATURE:
<223> OTHER INFORMATION: peptide fragments

<400> SEQUENCE: 7

Phe Ile Ala Trp Leu Val Lys Gly Arg Gly
1               5                   10

<210> SEQ ID NO 8
<211> LENGTH: 11
<212> TYPE: PRT
<213> ORGANISM: Artificial Sequence
<220> FEATURE:
<223> OTHER INFORMATION: peptide fragments

<400> SEQUENCE: 8

Phe Ile Ala Trp Leu Val Lys Gly Arg Gly Arg
1               5                   10

<210> SEQ ID NO 9
<211> LENGTH: 11
<212> TYPE: PRT
<213> ORGANISM: Artificial Sequence
<220> FEATURE:
```

```
<223> OTHER INFORMATION: peptide fragments

<400> SEQUENCE: 9

Phe Ile Ala Trp Leu Val Lys Gly Arg Gly Arg
1               5                   10

<210> SEQ ID NO 10
<211> LENGTH: 9
<212> TYPE: PRT
<213> ORGANISM: Artificial Sequence
<220> FEATURE:
<223> OTHER INFORMATION: peptide fragments

<400> SEQUENCE: 10

Phe Ile Ala Trp Arg Val Lys Gly Arg
1               5

<210> SEQ ID NO 11
<211> LENGTH: 9
<212> TYPE: PRT
<213> ORGANISM: Artificial Sequence
<220> FEATURE:
<223> OTHER INFORMATION: peptide fragments

<400> SEQUENCE: 11

Tyr Ile Ala Trp Leu Val Lys Gly Arg
1               5

<210> SEQ ID NO 12
<211> LENGTH: 13
<212> TYPE: PRT
<213> ORGANISM: Artificial Sequence
<220> FEATURE:
<223> OTHER INFORMATION: peptide fragments
<220> FEATURE:
<221> NAME/KEY: VARIANT
<222> LOCATION: 1, 13
<223> OTHER INFORMATION: Xaa = Any Amino Acid

<400> SEQUENCE: 12

Xaa Phe Tyr Ile Ala Trp Leu Val Lys Arg Gly Arg Xaa
1               5                   10

<210> SEQ ID NO 13
<211> LENGTH: 9
<212> TYPE: PRT
<213> ORGANISM: Artificial Sequence
<220> FEATURE:
<223> OTHER INFORMATION: peptide fragments

<400> SEQUENCE: 13

Arg Gly Lys Val Leu Trp Ala Ile Phe
1               5

<210> SEQ ID NO 14
<211> LENGTH: 10
<212> TYPE: PRT
<213> ORGANISM: Artificial Sequence
<220> FEATURE:
<223> OTHER INFORMATION: peptide fragments

<400> SEQUENCE: 14

Gly Arg Gly Lys Val Leu Trp Ala Ile Phe
1               5                   10

<210> SEQ ID NO 15
<211> LENGTH: 11
```

```
<212> TYPE: PRT
<213> ORGANISM: Artificial Sequence
<220> FEATURE:
<223> OTHER INFORMATION: peptide fragments

<400> SEQUENCE: 15

Arg Gly Arg Gly Lys Val Leu Trp Ala Ile Phe
 1               5                  10

<210> SEQ ID NO 16
<211> LENGTH: 7
<212> TYPE: PRT
<213> ORGANISM: Artificial Sequence
<220> FEATURE:
<223> OTHER INFORMATION: peptide fragments

<400> SEQUENCE: 16

His Trp Met Ala Trp Phe Lys
 1               5

<210> SEQ ID NO 17
<211> LENGTH: 6
<212> TYPE: PRT
<213> ORGANISM: Artificial Sequence
<220> FEATURE:
<223> OTHER INFORMATION: peptide fragments

<400> SEQUENCE: 17

Phe Ile Ala Trp Leu Val
 1               5

<210> SEQ ID NO 18
<211> LENGTH: 6
<212> TYPE: PRT
<213> ORGANISM: Artificial Sequence
<220> FEATURE:
<223> OTHER INFORMATION: peptide fragments

<400> SEQUENCE: 18

Phe Ile Glu Trp Leu Lys
 1               5

<210> SEQ ID NO 19
<211> LENGTH: 6
<212> TYPE: PRT
<213> ORGANISM: Artificial Sequence
<220> FEATURE:
<223> OTHER INFORMATION: peptide fragments

<400> SEQUENCE: 19

Phe Val Asn Trp Leu Leu
 1               5

<210> SEQ ID NO 20
<211> LENGTH: 6
<212> TYPE: PRT
<213> ORGANISM: Artificial Sequence
<220> FEATURE:
<223> OTHER INFORMATION: peptide fragments

<400> SEQUENCE: 20

Phe Val Gln Trp Leu Met
 1               5

<210> SEQ ID NO 21
<211> LENGTH: 7
<212> TYPE: PRT
```

```
<213> ORGANISM: Artificial Sequence
<220> FEATURE:
<223> OTHER INFORMATION: peptide fragments

<400> SEQUENCE: 21

Ala Tyr Gly Trp Met Asp Phe
1               5

<210> SEQ ID NO 22
<211> LENGTH: 6
<212> TYPE: PRT
<213> ORGANISM: Artificial Sequence
<220> FEATURE:
<223> OTHER INFORMATION: peptide fragments

<400> SEQUENCE: 22

His Trp Lys Trp Phe Lys
1               5

<210> SEQ ID NO 23
<211> LENGTH: 7
<212> TYPE: PRT
<213> ORGANISM: Artificial Sequence
<220> FEATURE:
<223> OTHER INFORMATION: peptide fragments

<400> SEQUENCE: 23

Tyr Met Gly Trp Met Asp Phe
1               5

<210> SEQ ID NO 24
<211> LENGTH: 6
<212> TYPE: PRT
<213> ORGANISM: Artificial Sequence
<220> FEATURE:
<223> OTHER INFORMATION: peptide fragments

<400> SEQUENCE: 24

Ser Met Leu Trp Met Asp
1               5

<210> SEQ ID NO 25
<211> LENGTH: 6
<212> TYPE: PRT
<213> ORGANISM: Artificial Sequence
<220> FEATURE:
<223> OTHER INFORMATION: peptide fragments

<400> SEQUENCE: 25

Leu Glu Gly Trp Leu His
1               5

<210> SEQ ID NO 26
<211> LENGTH: 6
<212> TYPE: PRT
<213> ORGANISM: Artificial Sequence
<220> FEATURE:
<223> OTHER INFORMATION: peptide fragments

<400> SEQUENCE: 26

Asp Ile Leu Trp Glu Val
1               5

<210> SEQ ID NO 27
<211> LENGTH: 10
<212> TYPE: PRT
<213> ORGANISM: Artificial Sequence
```

```
<220> FEATURE:
<223> OTHER INFORMATION: peptide fragments

<400> SEQUENCE: 27

Tyr Ile Ala Trp Leu Val Lys Gly Arg Gly
1               5                   10

<210> SEQ ID NO 28
<211> LENGTH: 10
<212> TYPE: PRT
<213> ORGANISM: Artificial Sequence
<220> FEATURE:
<223> OTHER INFORMATION: peptide fragments

<400> SEQUENCE: 28

Tyr Ile Ala Trp Leu Val Arg Gly Arg Gly
1               5                   10

<210> SEQ ID NO 29
<211> LENGTH: 10
<212> TYPE: PRT
<213> ORGANISM: Artificial Sequence
<220> FEATURE:
<223> OTHER INFORMATION: peptide fragments

<400> SEQUENCE: 29

Phe Ile Ala Trp Leu Val Arg Gly Arg Gly
1               5                   10

<210> SEQ ID NO 30
<211> LENGTH: 10
<212> TYPE: PRT
<213> ORGANISM: Artificial Sequence
<220> FEATURE:
<223> OTHER INFORMATION: peptide fragments
<220> FEATURE:
<221> NAME/KEY: VARIANT
<222> LOCATION: 7
<223> OTHER INFORMATION: Xaa = Lys or Arg
<220> FEATURE:
<221> NAME/KEY: VARIANT
<222> LOCATION: 10
<223> OTHER INFORMATION: Xaa = any amino acid or absent

<400> SEQUENCE: 30

Tyr Ile Ala Trp Leu Val Xaa Gly Arg Xaa
1               5                   10

<210> SEQ ID NO 31
<211> LENGTH: 10
<212> TYPE: PRT
<213> ORGANISM: Artificial Sequence
<220> FEATURE:
<223> OTHER INFORMATION: peptide fragments
<220> FEATURE:
<221> NAME/KEY: VARIANT
<222> LOCATION: 10
<223> OTHER INFORMATION: Xaa = any amino acid or absent

<400> SEQUENCE: 31

Phe Ile Ala Trp Leu Val Arg Gly Arg Xaa
1               5                   10

<210> SEQ ID NO 32
<211> LENGTH: 10
<212> TYPE: PRT
<213> ORGANISM: Artificial Sequence
<220> FEATURE:
<223> OTHER INFORMATION: peptide fragments
```

```
<220> FEATURE:
<221> NAME/KEY: VARIANT
<222> LOCATION: 10
<223> OTHER INFORMATION: Xaa = any amino acid or absent

<400> SEQUENCE: 32

Phe Ile Ala Trp Leu Val Lys Gly Arg Xaa
1               5                   10
```

C-TERMINAL FRAGMENTS OF GLUCAGON-LIKE PEPTIDE-1 (GLP-1)

CLAIM OF PRIORITY

This application is a divisional of U.S. patent application Ser. No. 13/127,387, filed Jul. 19, 2011, which is the national stage of International Application Number PCT/US2009/063746, filed on Nov. 9, 2009, which is based on and claims the benefit of U.S. Provisional Patent Application Ser. No. 61/112,341, filed on Nov. 7, 2008; Ser. No. 61/175,543, filed on May 5, 2009, and No. 61/181,849, filed on May 28, 2009, the entire contents of which are hereby incorporated by reference.

TECHNICAL FIELD

This invention relates to C-Terminal Fragments of Glucagon-Like Peptide-1 (GLP-1), and methods of use thereof, e.g., for the treatment of obesity and obesity-related disorders, e.g., diabetes and the metabolic syndrome.

BACKGROUND

Beta-oxidation is the metabolic process by which fatty acids, derived from fat by the actions of lipases, are converted to glucose via the formation of acetyl-CoA (Bebernitz and Schuster, Curr Pharm Des 8:1199-1227, 2002). A major source of Acetyl-CoA is fatty acid oxidation. Acetyl-CoA is a potent inhibitor of glucose oxidation via the activation of pyruvate dehydrogenase kinase (PDK), an inhibitor of the glycolytic enzyme pyruvate dehydrogenase complex (PDH-C). PDH is the rate limiting enzyme in the oxidation of glucose by converting pyruvate, derived from glucose in the glycolytic cycle, to Acety-CoA. A cardinal rule of energy metabolism is that glucose is the preferred fuel, the exception being the heart and brain that rely on FAO for 70% of their energy. When glucose becomes limited, such as in states of insulin resistance, the substrate for combustion is switched from glucose to fatty acids. This rule is known as the Randle Hypothesis (Diabetes Metab Rev 14:263-283, 1998). Importantly, according to the Randle hypothesis, inhibition of fatty acid metabolism (transport and/or oxidation) results in the stimulation of glucose oxidation and the inhibition of glucose production (gluconeogenesis). This is particularly important in the liver, the major site of gluconeogenesis.

SUMMARY

The present invention is based, at least in part, on the discovery that small C-terminal peptides of GLP-1 have the ability to reduce diet-induced obesity, likely as a result of inhibiting fatty acid oxidation in the mitochondria.

Thus, the invention includes peptides comprising nine or ten amino acids of the C-terminus of GLP-1, peptidomimetics thereof, and methods of using the peptides and peptidomimetics in treating obesity and obesity-related diseases such as diabetes and the metabolic syndrome.

Thus, in a first aspect, the invention provides isolated peptides consisting essentially of a sequence (Phe/Tyr)-Ile-Ala-Trp-Leu-Val-(Lys/Arg)-Gly-Arg-Xaa (SEQ ID NO:1), wherein Xaa can be Gly, Gly-Arg, Gly-Arg-Gly, or absent.

In some embodiments, if the C terminus is an Arg, the peptide is amidated. In some embodiments, one or more amino acids are modified by attachment of a fatty acid, e.g., palmitate or oleate.

In a further aspect, the invention provides fusion peptides comprising a first portion consisting essentially of a sequence: (Phe/Tyr)-Ile-Ala-Trp-Leu-Val-(Lys/Arg)-Gly-Arg-Xaa (SEQ ID NO:1), wherein Xaa can be Gly, Gly-Arg, Gly-Arg-Gly, or absent, fused to a cell-penetrating peptide. In some embodiments, the cell-penetrating peptide is fused on the C-terminus of the peptide. In some embodiments, the cell-penetrating peptide is selected from the group consisting of HIV-derived TAT peptide, penetratins, transportans, SS peptides, and hCT derived cell-penetrating peptides.

In yet another aspect, the invention provides isolated nucleic acids encoding the peptides or fusion peptides described herein, and host cells including and/or expressing the isolated nucleic acids.

In an additional aspect, the invention provides therapeutic compositions including the peptides or described herein in a physiologically acceptable carrier. In some embodiments, the compositions further include at least one cell-penetrating agent, e.g., a cationic liposome.

Also provided herein is the use of the peptides or fusion peptides described herein in the treatment of obesity or an obesity-related disorder. In some embodiments, the obesity-related disorder is diabetes or the metabolic syndrome.

In yet another aspect, the invention features methods for treating obesity or an obesity-related disorder in a subject. The methods include administering a therapeutically effective amount of a peptide or fusion peptide as described herein. In some embodiments, the obesity-related disorder is diabetes or the metabolic syndrome.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

The GLP-1 receptor complex (GLP-1RC) consists of three essential proteins: the GLP-1 G-protein-coupled receptor (GPCR), the fatty acid translocase/multifunctional receptor CD36/FAT, and the diaminopeptidyl peptidase CD26 (Dpp4). The GLP-1 receptor complex (GLP-1RC) regulates dual receptor functions: 1) activation of the cAMP-dependent Protein Kinase A pathway and 2) the fatty acid translocase CD36/FAT pathway resulting in an inhibition of fatty acid oxidation.

Insulinotropic GLP-1 agonists, such as GLP-1(7-36) amide, GLP-1(7-37), and exendin-4, bind to the GLP-1 GPCR with high affinity (nM) and activate the cAMP/PKA pathway resulting in the known cellular insulinotropic responses of GLP-1 (Kieffer and Habener, Endocr Revs 20:876-913, 1999; Drucker, Cell Metab 3:153-165, 2006). CD26 (Dpp4), a diaminopeptidyl peptidase, in the complex cleaves the insulinotropic hormome GLP-1(7-36)amide to the amino-terminally shortened insulinomimetic hormone GLP-1(9-36)amide (De Meester et al. Immunol Today 20:367-375, 1999; Lambeir et al. Crit Rev Clin Lab Sci 40:209-294, 2003). The GLP-1(9-36)amide, which is present at the receptor site in high concentrations (microM), may mimic a long chain fatty acid (LCFA) via an amphipathic alpha helix located in the C-terminal region (AKEFIAWLVKGRamide (SEQ ID NO:3) or AKEFIAWLVKamide (SEQ ID NO:4) or variants thereof), and is believed to bind to the complex-associated CD36/FAT receptor/fatty acid transporter. CD36/FAT may then transport the GLP-1(9-36) amide into endosomes, perhaps in association with a fatty acid binding protein.

Figure 1:
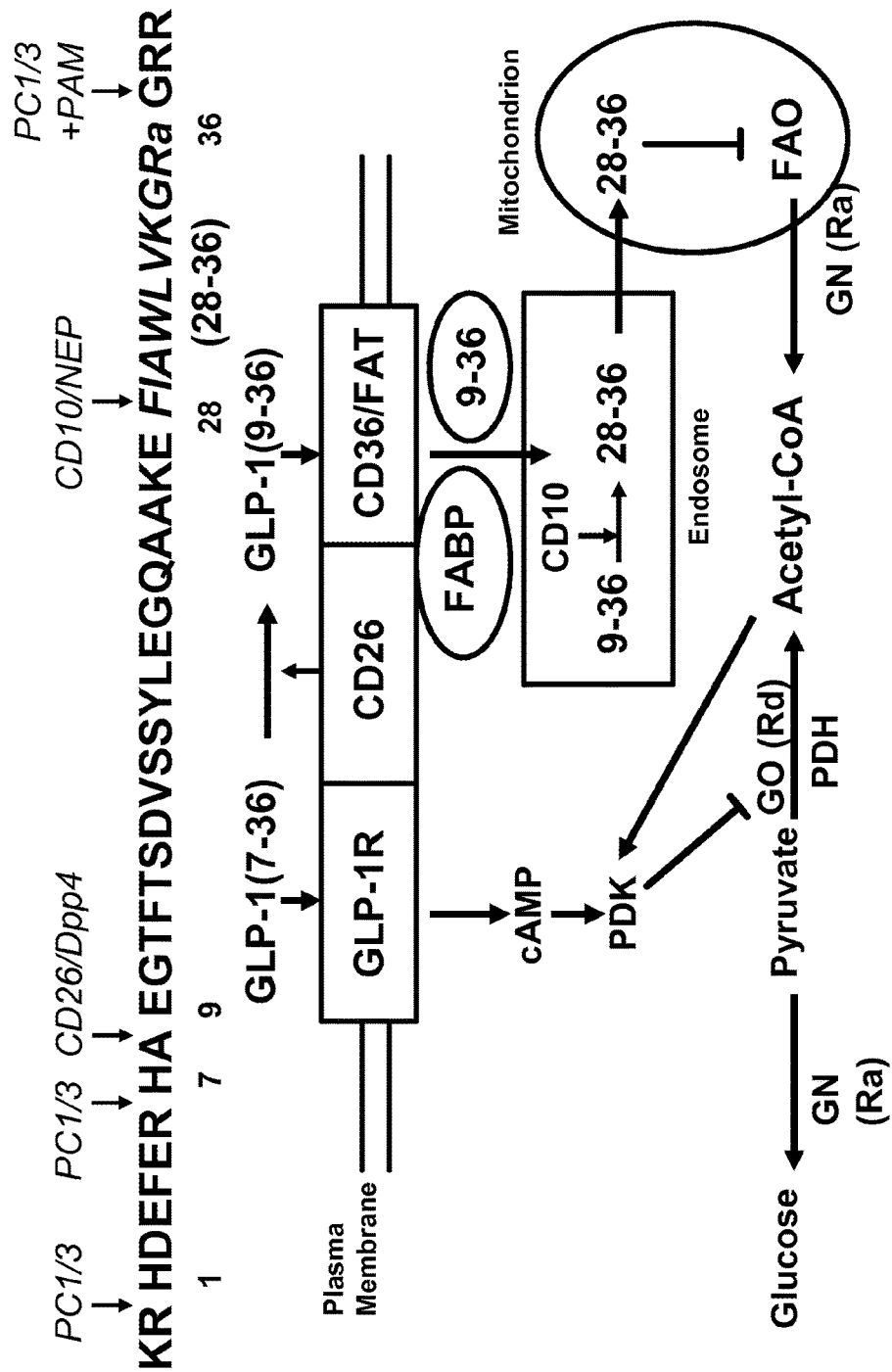
FIG. 1 is a model depicting a process in hepatocytes, and other insulin-sensitive tissues, through which GLP-1 (SEQ ID NO:2) undergoes two site-selective proteolytic cleavages resulting in the generation of a bioactive nonapeptide, GLP-1(28-36)amide resulting in the inhibition of fatty acid oxidation.

As described herein, it is believed that within the endosomes the GLP-1(9-36)amide is further cleaved by a neutral endopeptidase, such as NEP24.11, thereby liberating a C-terminal fragment of GLP-1(9-36)amide consisting of the amphipathic helical region envisioned, for example, to be GLP-1(28-36)amide, FIAWLVKGRamide (SEQ ID NO:5), or possibly, FIAWLVKamide (SEQ ID NO:6), or amino-terminally extended variants thereof, for example, AKEFAWLVKGRamide (SEQ ID NO:3) or AKEFIAWLVKamide (SEQ ID NO:4) (FIG. 1). The molecular structure of the GLP-1(28-36)amide mimics that of a medium/long chain fatty acid and is then acetylated by the enzyme Acetyl-CoA ligase on the free epsilon amino group of lysine in GLP-1 (28-36)amide (bolded in above depicted amino acid structures). The peptide so linked to acetyl-CoA is likely transported into the mitochondria (and peroixomes) where it is believed to be carried into and interacts with the enzymatic components involved in fatty acid oxidation, known as beta-oxidation, consisting of an enzymatic complex including the trifunctional protein consisting of the alpha and beta subunits, (HADHA and HADHB) (see FIG. 2). Since the GLP-1(9-36)amide is a LCFA mimetic, and the carbons are joined by peptide and now alkane linkages, it is poorly recognized by the fatty acid oxidation machinery and thereby inhibits beta-oxidation.

A hypothetical model, not meant to be binding, depicting the hypothesis that in hepatocytes, and other insulin-sensitive tissues, GLP-1 undergoes two site-selective proteolytic cleavages resulting in the generation of a bioactive nonapeptide, GLP-1(28-36)amide resulting in the inhibition of fatty acid oxidation is shown in FIG. 1. The model illustrates the concept that the parent insulinotropic hormone, GLP-1 (7-36)amide binds to high affinity G-protein coupled receptors (GLP-1R) in the plasma membrane, is cleaved by the adjacent diaminopeptidyl peptidase CD26 (Dpp-4) to yield the amino-terminal truncated insulinomimetic hormone GLP-1(9-36)amide which then binds to the lower affinity scavenger receptor CD36/FAT at the plasma membrane. GLP-1(9-36)amide is transported within the fatty acid transport pathway into the cell, in conjunction with a fatty acid binding protein (FABP) where it enters endosomes. The endosomes contain a neutral endopeptidase, presumed for example to be NEP24.11, also known as CD10 or CALLA, that cleaves GLP-1(9-36)amide into a carboxyl-terminal fragment peptide, GLP-1(28-36)amide. The GLP-1(28-36) amide mimics a fatty acid in its structure and is recognized by the AcylCoA ligase as a fatty acid that acylates GLP-1 (28-36)amide on the free epsilon amino group of the lysine at position 34. This peptide mimetic of a fatty acylCoA is carried into the core of the mitochondrion to the beta oxidation machinery where it interacts with the trifunctional protein. Since the peptide bonds of the GLP-1(28-36)amide cannot be cleaved to two carbon chains that constitute Acetyl-CoA, the product of the beta oxidation of fatty acids, it acts as an inhibitor of fatty acid oxidation (beta oxidation).

Figure 2:
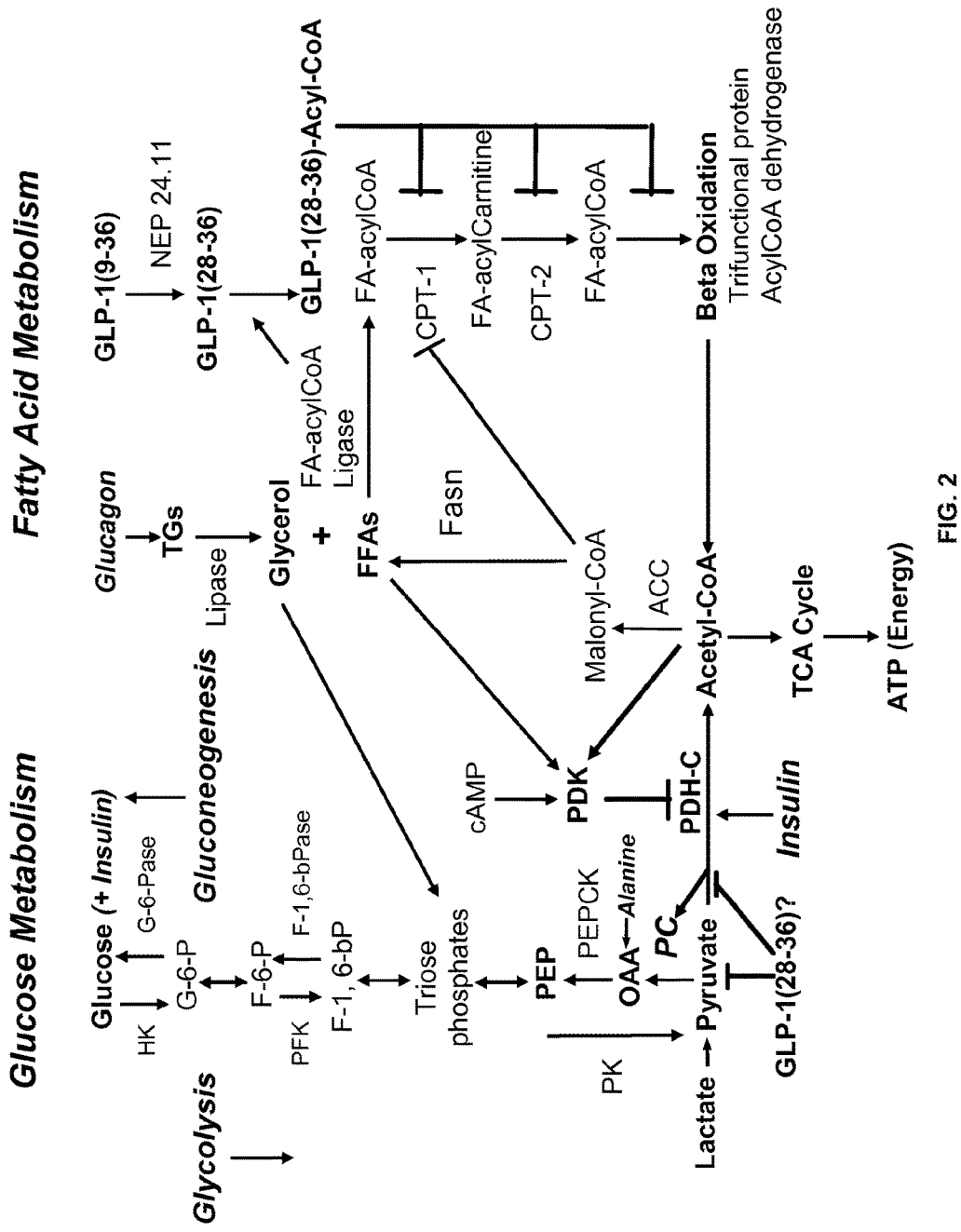
FIG. 2 is a diagram of the coupling of the glucose and fatty acid metabolic cycles in the liver (hepatocytes) and the proposed interaction of GLP-1 (9-36)amide in fatty acid metabolism (see FIG. 1). This diagram depicts the enzymatic pathways and cycles by which the fatty acid and glucose oxidation cycles are coupled.

A hypothetical illustration of the coupling of the glucose and fatty acid metabolic cycles in the liver (hepatocytes) and the proposed interaction of GLP-1 (9-36)amide in fatty acid metabolism is shown in FIG. 2, which depicts the enzymatic pathways and cycles by which the fatty acid and glucose oxidation cycles are coupled. Importantly: Acetyl-CoA is the energy currency that feeds the TCA cycle. Malonyl-CoA is a potent inhibitor of fatty acid oxidation. Acetyl-CoA is an activator of pyruvate dehydrogenase kinase (PDK) which is a potent inhibitor of the pyruvate dehydrogenase complex (PDHC), the major enzyme responsible for glucose oxidation. Moreover, Acetyl-CoA is a potent activator of pyruvate carboxylase (PC) the important first step in the utilization of pyruvate to produce glucose in the gluconeogenic pathway, the reverse of the glycolytic/glucose oxidation pathway. Insulin is the major hormonal activator of PDHC (glucose oxidation). Simply stated, the glucose oxidation and fatty acid oxidation pathways are coupled. In conditions in which glucose oxidation is limited such as during fasting, and/or states of insulin resistance/deficiency, and elevated glucagon levels, fatty acid oxidation is increased and the glucose oxidation (glycolytic cycle) is reversed to that of glucose production (gluconeogenesis).

Neutral Endopeptidase-24.11 (NEP24.11, CD10)

The proposed cleavage of GLP-1 (9-36) in the endosomes by neutral endopeptidases such as NEP24.11/CD10 is expected to form C-terminal fragments of approximately 9 to 12 amino acids consisting of the amphipathic alpha helix, still bound to CD36/FAT. This cleavage is analogous to the cleavage of glucagon to miniglucagon, as reported by Authier et al. (Endocrinology 144:5353-5364, 2003). Since the GLP-1 C-terminal fragment is likely acting as a surrogate LCFA it is not effective as LCFA and thus has a net inhibitory action on the functions of CD36 in fatty acid (LCFA) transport and oxidation (Koonen et al., Diabetes 56:2863-2871, 2007). Hupe-Sodmann et al. (Regul Pept 58:149-156, 1995) showed that the neutral endopeptidase, NEP24.11 readily cleaves GLP-1(7-36)amide in vitro to a C-terminal peptide with the sequence, FIAWLVKGRamide (SEQ ID NO:5) (see Table 2 on page 153 of Hupe-Sodmann et al.). Moreover, the endopeptidase NEP24.11 is widely distributed in tissues throughout the body (Rogues et al., Pharmacol Rev 45:87-146, 1993). As described herein, infusion of the GLP-1 C-terminal peptides inhibited weight gain in mice fed a high fat diet.

Common Shared C-Terminal Amphiphilic Helical Coiled-Coil Regions in Several Peptide Hormones Graham Baldwin and coworkers describe the binding of C-terminal gastrin peptides to HADHA, the 78 kDa alpha subunit of the trifunctional protein, which is the heart of the beta oxidation enzymatic complex (Murphy et al., Int J Biochem Cell Biol 28:1233-1240, 1996). Gastrin C-terminal peptides bind to and inhibit both the alpha and beta subunits of the trifunctional protein involved in fatty acid oxidation. (Hashimoto et al., J Biochem 119:1196-1201, 1996). Early on it was believed that HADHA was the gastrin receptor. Subsequently, a G-protein coupled receptor (GPCR) was identified for gastrin, and for CCK, and the significance of HADHA and the trifunctional protein in gastrin interactions has remained unknown. Gastrin is reported to stimulate epithelial-mesenchymal transitions of cells (Ferrand et al., Exp Cell Res 301:128-138, 2004). As of now no connection has yet been made between gastrin/CCK and CD36. The actions of gastrin that occur independently of its GPCR are referred to as mediated by a "novel" receptor. Interestingly, the C-terminal pentapeptide sequence shares strong amino acid sequence similarities with the similar region in GLP-1, and several other peptide hormones including exendin-4, gastric inhibitory polypeptide (GIP), glucagon, growth hormone-releasing peptide (GHRP), cholecystokinin (CCK), ghrelin, and the synthetic growth hormone secretagogue (hexarelin) (see Table 4).

GLP-1 C-Terminal Peptides, Fusion Peptides, Peptidomimetics, and Modifications

The GLP-1 C-terminal peptides described herein include the sequence FIAWLVKGRamide (SEQ ID NO:5), or a variant thereof. Variants include peptides in which the sequence is C-terminally extended, e.g., FIAWLVKGRG (SEQ ID NO:7), FIAWLVKGRGR (SEQ ID NO:8), or FIAWLVKGRGRamide (SEQ ID NO:9), or in which one or more amino acids are conservatively substituted, for example FIAWRVKGRamide (SEQ ID NO:10), in which Lysine 32 (the numbering refers to the full-length GLP-1) is changed to Arginine, or in which Phenylalanine 28 is changed to Tyrosine (YIAWLVKGRamide (SEQ ID NO:11)). In some embodiments the peptides also include the sequence AKE on the N-terminus.

Thus in some embodiments, the peptides described herein can have the sequence

Xaa$_1$-(Phe/Tyr)-Ile-Ala-Trp-Leu-Val-(Lys/Arg)-Gly-Arg-Xaa$_2$ (SEQ ID NO:12), wherein Xaa$_1$ can be Ala-Lys-Glu, or absent, and Xaa$_2$ can be Gly, Gly-Arg, Gly-Arg-Gly, or absent.

In some embodiments, the peptides described herein can have the sequence (Phe/Tyr)-Ile-Ala-Trp-Leu-Val-(Lys/Arg)-Gly-Arg-Xaa (SEQ ID NO:1),
wherein Xaa can be Gly, Gly-Arg, Gly-Arg-Gly, or absent.

Methods for making these peptides are known in the art, e.g., using chemical synthesis or expression in a host cell.

Fusion Peptides

In some embodiments, the peptides also include a cell-penetrating moiety that facilitates delivery of the peptides to the intracellular space, e.g., HIV-derived TAT peptide, penetratins, transportans, SS peptides (alternating aromatic residues and basic amino acids (aromatic-cationic peptides)), SA, SM, or SNL peptides, or hCT derived cell-penetrating peptides, see, e.g., Caron et al., (2001) Mol Ther. 3(3):310-8; Langel, *Cell-Penetrating Peptides: Processes and Applications* (CRC Press, Boca Raton Fla. 2002); El-Andaloussi et al., (2005) Curr Pharm Des. 11(28):3597-611; Lindgren et al., Trends Pharmacol Sci. 21(3):99-103 (2000); Zhao et al., J Biol Chem 279:34682-34690 (2004); Szeto, AAPS Journal 2006; 8 (2) Article 32; Deshayes et al., (2005) Cell Mol Life Sci. 62(16):1839-49; Hom et al., J Med. Chem., 46:1799 (2003); Bonny et al., Diabetes, 50:77-82 (2001), and U.S. Pat. Nos. 6,841,535 and 7,576,058 and references cited therein. In some embodiments the cell-penetrating moiety is linked to the peptide, e.g., as a single fusion protein; thus, the invention includes fusion proteins comprising a GLP-1 C-terminal peptide as described herein and a cell-penetrating peptide, e.g., TAT, penetratins, transportans, or hCT derived cell-penetrating peptides. In some embodiments, the cell-penetrating peptide is attached to the N-terminus of the GLP-1 C-terminal peptide; in some embodiments, the cell-penetrating peptide is attached to the C-terminus of the GLP-1 C-terminal peptide. In some embodiments, the fusion protein further comprises a cleavable moiety as known in the art between the cell-penetrating peptide and the GLP-1 C-terminal peptide, that cleaves off the cell-penetrating peptide, leaving the GLP-1 C-terminal peptide intact.

Peptidomimetics

In some embodiments, the peptides disclosed herein can be modified according to the methods known in the art for producing peptidomimetics. See, e.g., Kazmierski, W. M., ed., Peptidomimetics Protocols, Human Press (Totowa N.J. 1998); Goodman et al., eds., Houben-Weyl Methods of Organic Chemistry: Synthesis of Peptides and Peptidomimetics, Thiele Verlag (New York 2003); and Mayo et al., J. Biol. Chem., 278:45746 (2003). In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N terminus to the C terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetics include replacing one or more amino acid residues in a peptide with a chemically distinct but recognized functional analog of the amino acid, i.e., an artificial amino acid analog. Artificial amino acid analogs include beta-amino acids, beta-substituted beta-amino acids ("beta3-amino acids"), phosphorous analogs of amino acids, such as -amino phosphonic acids and -amino phosphinic acids, and amino acids having non-peptide linkages. Artificial amino acids can be used to create peptidomimetics, such as peptoid oligomers (e.g., peptoid amide or ester analogues), beta-peptides, cyclic peptides, oligourea or oligocarbamate peptides; or heterocyclic ring molecules. Exemplary retro-inverso peptidomimetics include RGKVLWAIF (SEQ ID NO:13), GRGKVLWAIF (SEQ ID NO:14), or RGRGKVLWAIF (SEQ ID NO:15), wherein the sequences include all D-amino acids.

Modifications

The peptide sequences described herein can be modified, e.g., by modification of one or more amino acid residues of a peptide by chemical means, either with or without an enzyme, e.g., by alkylation, acylation, ester formation, amide formation, e.g., at the carboxy terminus, or biotinylation, e.g., of the amino terminus. In some embodiments, the peptides are modified by the addition of a lipophilic substituent (e.g., a fatty acid) to an amino acid, e.g., to the Lysine. In some embodiments, the peptides include one or more of an N-terminal imidazole group, or a C-terminal amide group. In some embodiments, the epsilon-amino group of Lys34 is substituted with a lipophilic substituent, e.g., of about 4-40 carbon atoms, e.g., 8-25 carbon atoms. Examples include branched and unbranched C6-C20 acyl groups. Exemplary lipophilic substituents, and methods of attaching the same (including via an optional linker) are provided in U.S. Pat. No. 6,268,343 and Knudsen et al., J. Med. Chem. 43:1664-1669 (2000). In some embodiments, the lipophilic substituent is a fatty acid selected from the group consisting of straight-chain or branched fatty acids, e.g., oleic acid, caprylic acid, palmitic acid, and salts thereof.

In some embodiments, the peptide sequences are modified by substituting one or more amino acid residues of the parent peptide with another amino acid residue. In some embodiments, the total number of different amino acids between the sequence-modified peptide and the corresponding native form of the GLP-1 C-terminal peptide is up to five, e.g., up to four amino acid residues, up to three amino acid residues, up to two amino acid residues, or one amino acid residue.

In some embodiments, the total number of different amino acids does not exceed four. In some embodiments, the number of different amino acids is three, two, or one. In order to determine the number of different amino acids, one should compare the amino acid sequence of the sequence-modified GLP-1 peptide derivative with the corresponding native GLP-1 C-terminal fragment.

A number of suitable GLP-1 sequence analogues and modifications are described in the art, see, e.g., EP 0708179; WO 91/11457; U.S. Pat. No. 6,268,343)

Nucleic Acids, Vectors, and Host Cells

In one aspect, the invention includes nucleic acids encoding a GLP-1 C terminal peptide or modified peptide as described herein. For example, the invention includes nucleic acids encoding peptides that include the sequence SEQ ID NO:1 or 12. Nucleic acids disclosed herein also include nucleic acids encoding certain modified GLP-1 C-terminal peptides, e.g., retro-GLP-1 C-terminal peptides, GLP-1 C-terminal peptides linked to a cellular internalization (carrier) sequence, and retro-GLP-1 C-terminal peptides linked to a carrier sequence.

Nucleic acids disclosed herein also include both RNA and DNA, including genomic DNA and synthetic (e.g., chemically synthesized) DNA. Nucleic acids can be double-stranded or single-stranded. Nucleic acids can be synthesized using oligonucleotide analogs or derivatives (e.g., inosine or phosphorothioate nucleotides). Such oligonucleotides can be used, for example, to prepare nucleic acids with increased resistance to nucleases.

Also included in the invention are genetic constructs (e.g., vectors and plasmids) that include a nucleic acid encoding a peptide described herein operably linked to a transcription and/or translation sequence that enables expression of the peptide, e.g., expression vectors. A selected nucleic acid, e.g., a DNA molecule encoding a peptide described herein, is "operably linked" to another nucleic acid molecule, e.g., a promoter, when it is positioned either adjacent to the other molecule or in the same or other location such that the other molecule can direct transcription and/or translation of the selected nucleic acid.

Also included in the invention are various engineered cells, e.g., transformed host cells, which contain a nucleic acid disclosed herein. A transformed cell is a cell into which (or into an ancestor of which) has been introduced, by means of recombinant DNA techniques, a nucleic acid encoding an a peptide described herein that binds HSP-90 and/or induces apoptosis in a tumor cell. Both prokaryotic and eukaryotic cells, e.g., mammalian cells (e.g., tumor cell), yeast, fungi, and bacteria (such as *Escherichia coli*), can be host cells. An engineered cell exemplary of the type included in the invention is a tumor cell that expresses a GLP-1 C-terminal peptide.

Methods of Treatment

The methods described herein include methods for the treatment of obesity and disorders associated with obesity, e.g., diabetes and metabolic syndrome. In some embodiments, the disorder is diet-induced obesity, e.g., high-calorie or high-fat diet induced obesity. Generally, the methods include administering a therapeutically effective amount of a GLP-1 C-terminal peptide or peptidomimetic as described herein, to a subject who is in need of, or who has been determined to be in need of, such treatment.

As used in this context, to "treat" means to ameliorate at least one symptom of obesity or a disorder associated with obesity. Often, obesity results in hyperglycemia; thus, a treatment can result in a reduction in blood glucose levels and a return or approach to normoglycemia. Administration of a therapeutically effective amount of a compound described herein for the treatment of obesity will result in decreased body weight or fat.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the 1050 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical Compositions and Methods of Administration

The methods described herein include the manufacture and use of pharmaceutical compositions, which include GLP-1 C-terminal peptides described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

In some embodiments, the GLP-1 C-terminal peptides are formulated with a cell penetrating agent as known in the art, e.g., liposomes or micelles. Biodegradable microparticle or nanoparticle delivery systems that increase intracellular uptake, e.g., polymeric and surface modified nanoparticles as described in US 2009/0136585 and, can also be used. Examples include poly DL-lactide-co-glycolide (PLGA) nanoparticles, e.g., surface-modified with known surface-modifying agents, such as heparin, dodecylmethylammonium bromide (DMAB), DEAE-Dextran, lipofectin, and fibrinogen (see, e.g. Song et al., J. Control. Release, 54:201-211 (1998); Labhasetwar et al., J. Pharm. Sci., 87:1229-34 (1998); Lee et al., Biomaterials 29(9):1224-1232 (2008); and US 2009/0136585.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims.

Example 1. GLP-1 Cross-Linked Proteins

Proteins cross-linked by GLP-1(7-36) with a fluorescent label (FITC) at the C-terminal region in 3T3-L1 adipocytes were analyzed. The cross-linked proteins were fractionated by SDS-PAGE and fluorescent-labeled proteins were isolated and subjected to protein analyses and identification of MALDI-TOF mass spectrometry using standard methodology.

Essentially all of the proteins, some 20+ of them, were components of the fatty acid transport and oxidation machinery. The proteins identified by these methods and known to be involved in fatty acid transport and oxidation are listed in Table 1.

TABLE 1

Proteins Involved in Fatty Acid Transport and Oxidation Cross-Linked by GLP-1(7-36) in 3T3-L1 Adipocytes Long chain fatty acid CoA ligase 1
HADHA trifunctional protein alpha
HADHB trifunctional protein beta
Succinate dehydrogenase ubiquinone flavoprotein
Acyl CoA dehydrogenase 9
3-hydroxyacyl CoA dehydrogenase type II
Aldehyde dehydrogenase 6
NADH ubiquinone oxidoreductase 75 kDa
Solute carrier 27a4 fatty acids
Acyl CoA dehydrogenase very long chain specific
Carnitine palmitoyl transferase 2
Acyl CoA desaturase
Acyl CoA dehydrogenase, short/branched chain specific
Acyl CoA dehydrogenase, medium chain specific
Fatty acid CoA ligase long chain 6
Methylcrotonyl CoA carboxylase 2
Dehydrogenase/reductase SDR1
Putative steroid dehydrogenase
Succinyl CoA ligase beta
Fatty aldehyde dehydrogenase-like
Acetyl Coenzyme A carboxylase
Serine palmitoyltransferase 1
Pyruvate carboxylase Notably, GLP-1 strongly cross-linked the two subunits of the trifunctional protein (HADHA and HADHB), which are enzymes located in the matrix of mitochondria that comprise the core of the beta oxidation machinery, as well as several enzymes involved in mitochondrial fatty acid transport and metabolism, such as AcylCoA dehydrogenases, AcylCoA ligase, and carnitine palmitoyl transferase 2; carnitine palmitoyl transferase 2 and the AcylCoA dehydrogenases are located in the inner membrane of mitochondria. It is likely that Dpp4 present in the 3T3 cells processed the labeled GLP-1(7-36)amide to GLP-1(9-36)amide quite effectively. Notably, 3T3-L1 adipocytes use up glucose from the culture media at a very high rate (Carlson et al., Mol Cell Biol. 13(8):4736-44 (1993)) so that these cells are likely glucose-deprived at the time of the incubation with GLP-1(7-36) amide and the cross-linking. Furthermore, the adipocytes contain high amounts of stored triglyceride that serves as the substrate for fatty acid oxidation.

The results showed that peptides including the C-terminus of GLP-1 cross-link predominantly to mitochondrial proteins involved in fatty acid transport and oxidation.

These results implicate an action of GLP-1 or fragments thereof in fatty acid oxidation.

Example 2. Glucagon-Like Peptide-1 Carboxyl-Terminal Nonapeptide, GLP-1(28-36)amide, Prevents Weight Gain in High Fat Fed Mice Glucagon-like peptide-1 (GLP-1) is an insulinotropic peptide that stimulates glucose-dependent insulin secretion (Kieffer and Habener, Endocr Rev. 20(6):876-913 (1999)). The insulinotropic peptide, GLP-1(7-36)amide is rapidly inactivated in the circulation by the diaminodipeptidyl peptidase-4 (Dpp4) to give the GLP-1(9-36)amide (Drucker, Cell Metab. 3(3):153-65 (2006)). GLP-1 agonists, and inhibitors of Dpp4 to enhance plasma levels of endogenous insulinotropic GLP-1(7-36)amide, are in use for the treatment of type 2 diabetes (Lovshin et al., Nat Rev Endocrinol.

Figure 3:
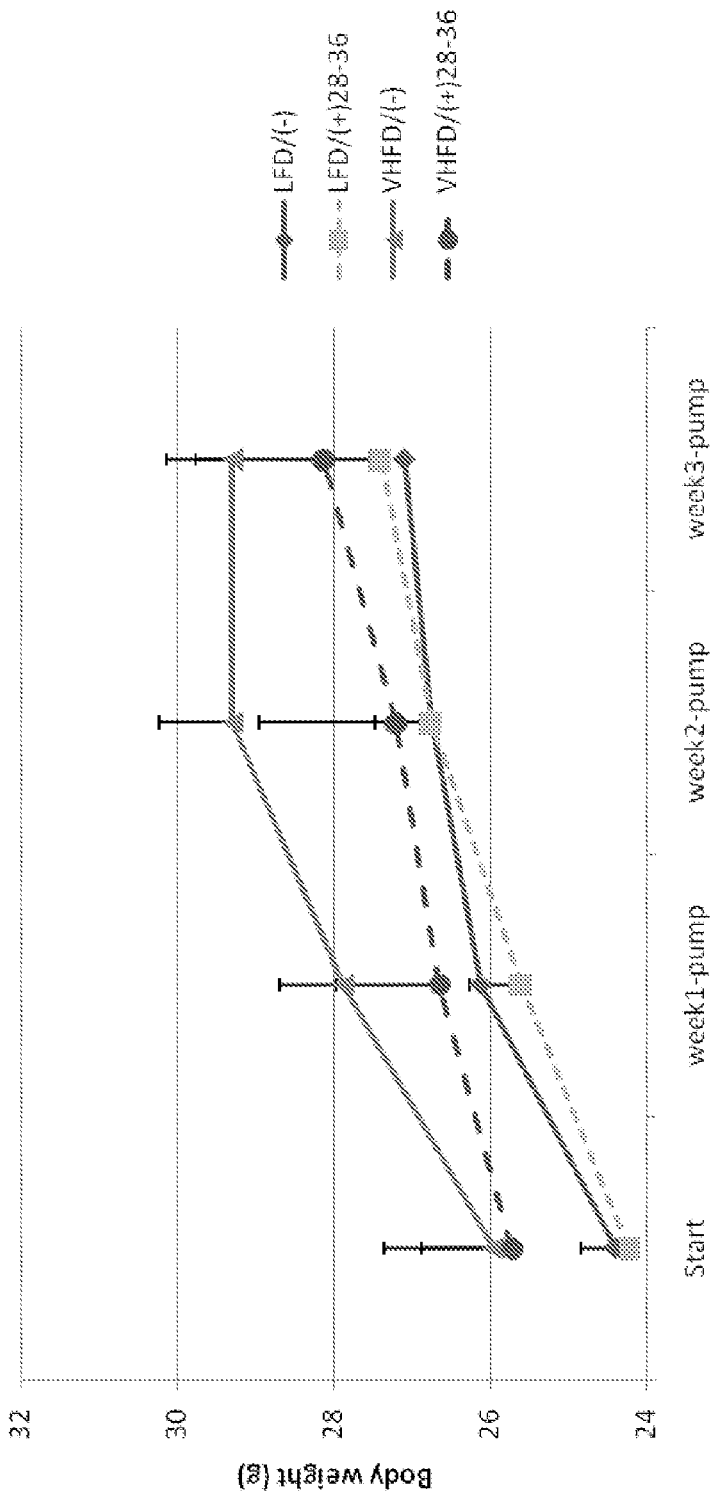
FIG. 3 is a line graph showing that the results of infusion of GLP-1(28-36) in mice fed a very high fat diet (VHFD, 60% fat) attenuates weight gain. Mice were placed on VHFD or a LFD control diets at 6 weeks of age. Continuous infusion of GLP-1(28-36)amide, 6.5 nanomoles/24 hrs/KgBW via osmopumps was started at ten weeks of age and was continued for 3 weeks. Body weights were measured before and during these three weeks. Values are means and S.D.s of four mice in each group.

5(5):262-9 (2009)). Although the GLP-1(9-36)amide metabolite is generally believed to be biologically inactive, recent evidence indicates that it exerts cardioprotective actions (Ban et al., Circulation. 117(18):2340-50 (2008)) and inhibits hepatic glucose production (gluconeogenesis) (Elahi et al., Obesity (Silver Spring). 16(7):1501-9 (2008)). Because in preliminary studies in isolated hepatocytes we found only weak actions of GLP-1(9-36)amide at high (micromolar) concentrations on hepatic gluconeogenesis, it was hypothsized that GLP-1(9-36)amide could be a precursor of a smaller active peptide encoded within the amino acid sequence of GLP-1(9-36)amide. The neutral endopeptidase, NEP 24.11 is proposed to be responsible for the degradation of GLP-1, much as the Dpp4 had been thought of as a peptide degrading enzyme for GLP-1 (Plamboeck et al., Diabetologia. 48(9):1882-90 (2005)). The carboxyl-terminal sequence of GLP-1, FIAWLVKGRamide, GLP-1(28-36)amide, is a major peptide product of the cleavage of GLP-1 by NEP 24.11 (Hupe-Sodmann et al., Regul Pept. 58(3):149-56 (1995)). Therefore GLP-1(28-36)amide was infused into mice both fed a normal chow diet (LFD) and a very high fat diet (VHFD) for three weeks. Remarkably, GLP-1(28-36)amide completely prevented the normal weight gain and adipogenesis seen in the high fat fed mice without observable differences in food intake (see FIG. 3).

An examination of gene expression profiles in the livers of GLP-1(28-36)amide treated mice was performed. Measurements of mRNA levels by quantitative polymerase chain reaction (QPCR) in livers of mice given a very high fat diet (VHFD) or a normal low fat diet (LFD) for four weeks followed by subcutaneous osmopump infusions of either vehicle or GLP-1(28-36)amide for three additional weeks. Data in Table 2, below, show changes in mRNA levels in LFD and VHFD groups of mice comparing vehicle versus GLP-1(28-36)amide where vehicle is set at a value of 1.0. Table 3 shows the data normalized to the LFD mice as 1.0. Major changes in mRNA levels were seen for PEPCK (phosphopyruvate carboxykinase), PPARgamma (Peroxisome proliferation activation receptor gamma), CD36 (cCuster determinant 36/fatty acid translocater), SCD-1 (Sterol CoA dehydrogenase), SREB1P1c (Steroid response element binding protein 1c), FASN (Fatty acid synthase), and PPARalpha (Peroxisome proliferation activator receptor alpha). GLP-1(28-36)amide appears to regulate PEPCK, PPARg, CD36, SCD1, SREBP1c, FASN, and PPARa.

The results demonstrated that the peptide (28-36) regulated of the mRNAs for Steroyl CoA saturase, Carnitine palmitoyl transferase 1, AcylCoA oxidase. AcylCoA carboxylase, Fatty acid synthase, and Phosphopyruvate carboxykinase and protein and phospho-protein levels of AcetylCoA carboxylase, suggesting modulation of fatty acid oxidation (see Tables 2 and 3).

TABLE 2

Fold Difference compared to PEPTIDE (28-36)

| mRNA/QPCR | LFD | LFD/28-36 | VHFD | VHFD/28-36 |
|---|---|---|---|---|
| PEPCK | 1 | 1.6 | 1 | 1.5 |
| ACOX | 1 | 1.4 | 1 | 1.04 |
| PPARγ | 1 | 1.54 | 1 | 1.4 |
| PGC1α | 1 | 1.4 | 1 | 1.2 |
| CD36 | 1 | 1.25 | 1 | 1.7 |
| SCD-1 | 1 | (2) | 1 | 3.05 |
| CPT1 | 1 | 1.21 | 1 | 1.02 |
| SREBP-1c | 1 | 1.1 | 1 | 1.3 |
| FASN | 1 | 1 | 1 | 1.2 |
| PPARα | 1 | 1.2 | 1 | 1.35 |

Values in parentheses indicate down-regulation.

TABLE 3

Fold Difference compared to LFD

| mRNA/QPCR | LFD | LFD/28-36 | VHFD | VHFD/28-36 |
|---|---|---|---|---|
| PEPCK | 1 | 1.6 | 1.07 | 1.6 |
| ACOX | 1 | 1.4 | 1.14 | 1.2 |
| PPARγ | 1 | 1.54 | 1.6 | 2.2 |
| PGC1α | 1 | 1.35 | (1.7) | (1.4) |
| CD36 | 1 | 1.25 | 1 | 1.7 |
| SCD-1 | 1 | (2) | (50) | (15) |
| CPT1 | 1 | 1.2 | 1.7 | 1.74 |
| SREBP-1c | 1 | 1 | (1.2) | 1 |
| FASN | 1 | 1 | (5) | (4) |
| PPARα | 1 | 1.2 | 1.4 | 1.9 |

Values in parentheses indicate down-regulation.

Figure 4A:
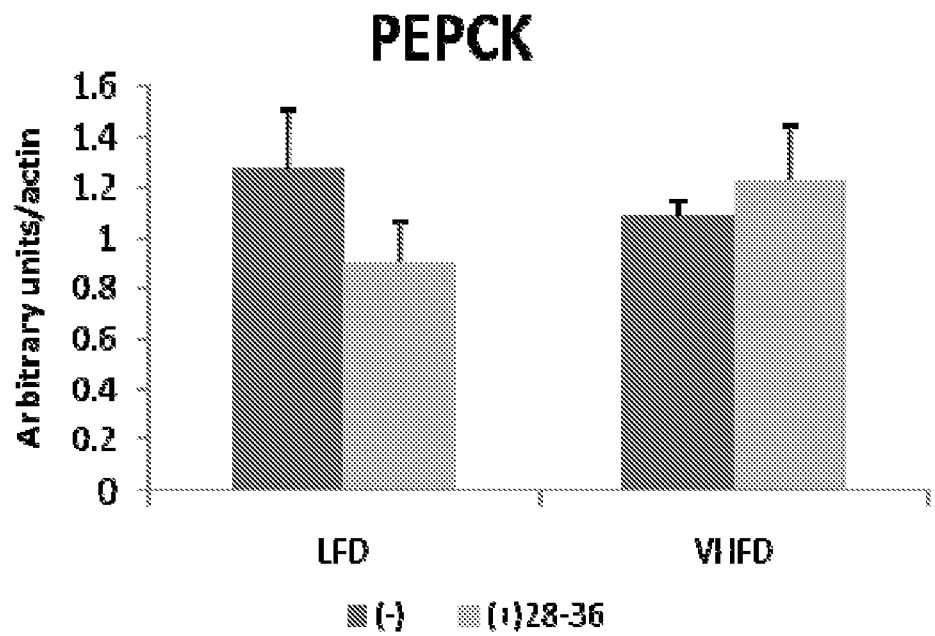
FIGS. 4A-4C are bar graphs showing regulation of PEPCK (4A) and ACC Protein Expression (both the phosphorylated (pACC) and unphosphorylated (ACC) forms (4B) in the presence and absence of the GLP-1(28-36) peptide, as well as the effect of the peptide on ratios of phosphorylated to unphosphorylated ACC (4C).
Figure 4B:
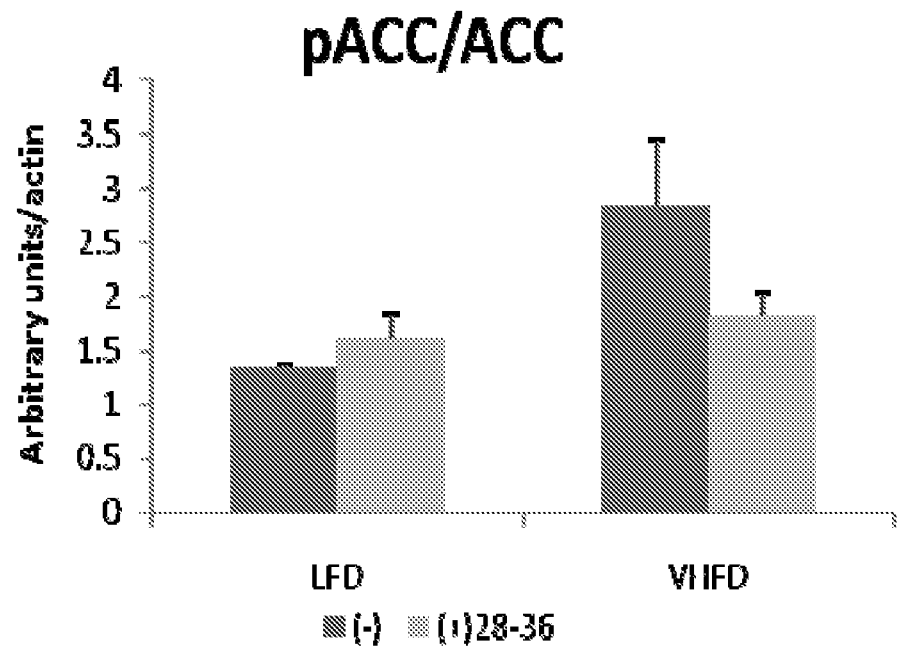
Figure 4C:
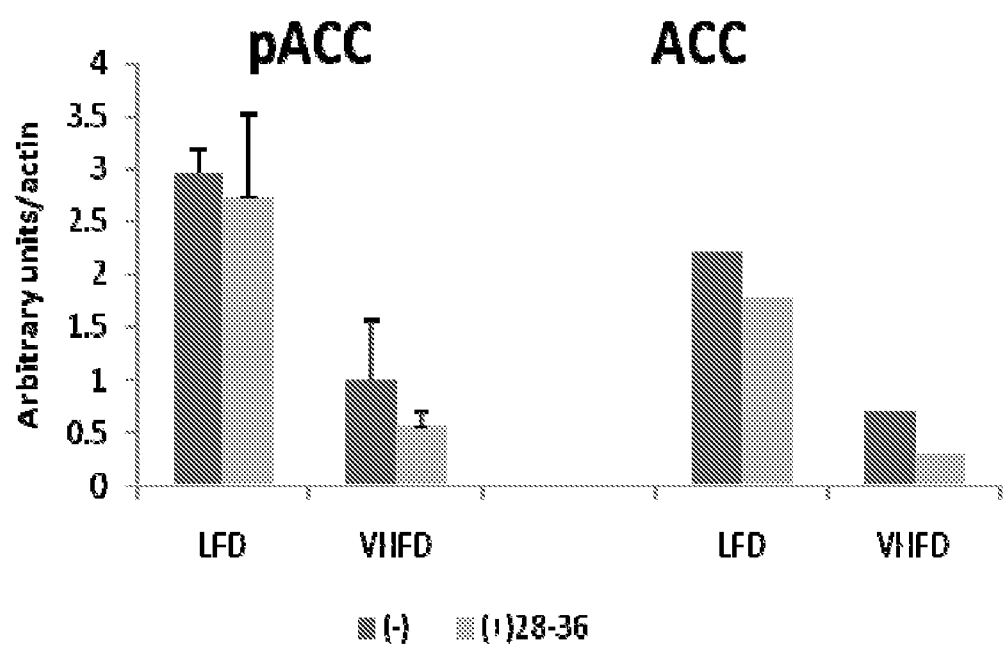
Figure 5:
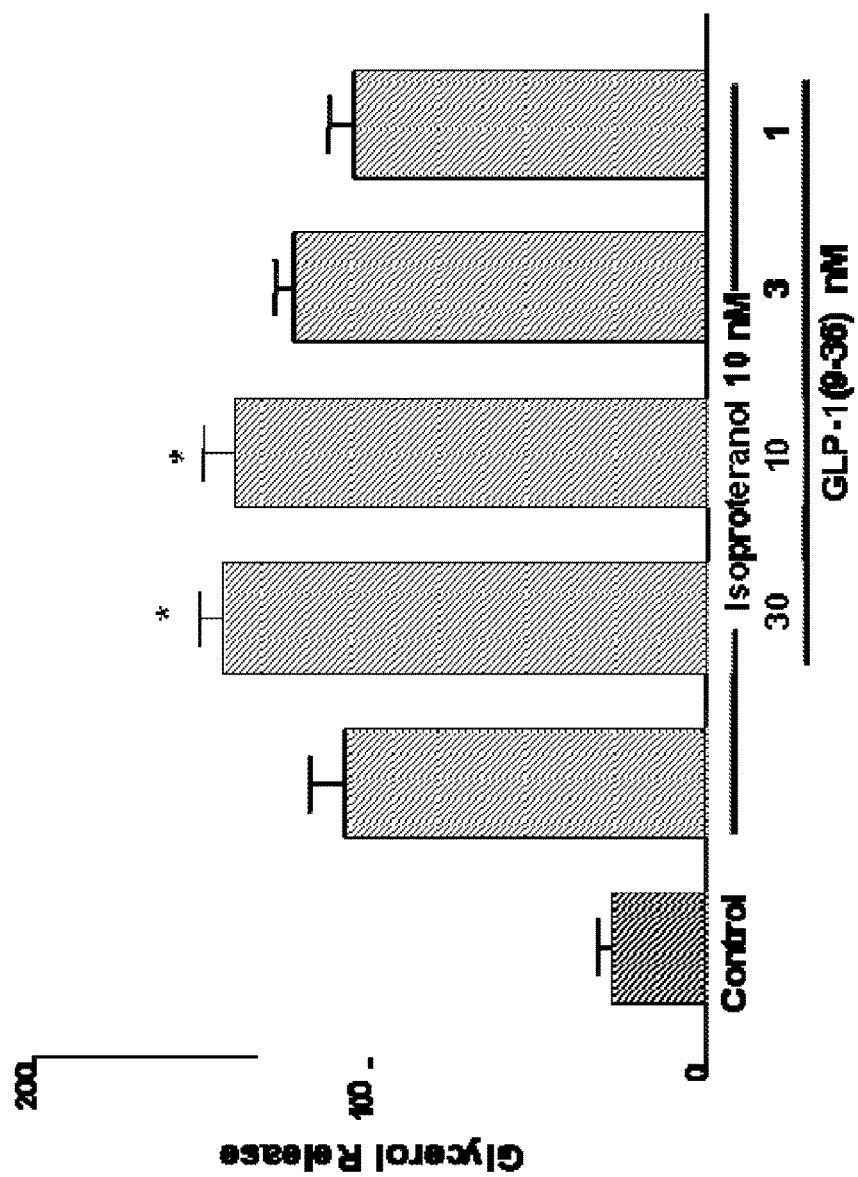
FIG. 5 is a bar graph showing that GLP-1(9-36)amide stimulates lipolysis in 3T3-L1 adipocytes in a dose dependent manner.

As shown in FIGS. 4A-4C, infusion of GLP-1(28-36) amide for three weeks in mice fed a very high fat diet resulted in a decrease in liver phosphoACC (pACC, phospho-AcetylCoA carboxylase), see, e.g., FIG. 4C, indicating an increase in ACC bioactivity (phosphorylation of ACC inactivates enzyme activity). This is important since ACC is highly regulated in the liver and is the key enzyme responsible for the synthesis of malonyl CoA from AcetylCoA and is a precursor of fatty acid synthesis and a potent inhibitor of CPT1 (carnitine palmitoyl transferase 1), the rate limiting enzyme in the transport of fatty acids into the beta oxidation machinery of mitochondria. This means that GLP-1(28-36) is exerting an inhibition on fatty acid oxidation (beta oxidation). The increase in SCD1 expression in response to infusion of GLP-1(28-36)amide is consistent with an increase in ACC activity since SCD1 is believed to inhibit AMP kinase which is an inhibitor of ACC. The mechanism currently proposed for the prevention of weight gain by GLP-1(28-36)amide in mice fed a very high fat diet involves a dual effect of GLP-1(28-36)amide on adipose tissue to enhance lipolysis and fat burning and inhibit lipogenesis. The increased fatty acid cycling and hypertriglyceridemia enhances hepatic fatty acid oxidation with consequent coupled enhanced gluconeogenesis driven by the enhanced fat burning. PEPCK expression is under complex feedback control and is a measure of gluconeogenesis Preliminary studies on the effect of GLP-1(9-36) on lipolysis were also performed in isolated mouse hepatocytes and 3T3-L1 adipocytes. Glycerol release into the culture medium was used as a measure of active lipolysis, and isoproterenol serves as a known stimulator of lipolysis. In these experiments GLP-1(9-36)amide was added dose-wise (1-30 nM) on a background of 10 nM isoproterenol. Incubations were for 60 min. The results, shown in FIG. 5, indicate that GLP-1(28-36)amide targets to mitochondria and exerts a fat burning phenotype by inhibiting lipogenesis, and stimulating lipolysis, suggesting processing of GLP-1 (9-36)amide to GLP-1(28-36)amide in adipocytes.

GLP-1(7-36)amide with a fluorescent label (FITC) at the C-terminal region cross-linked mitochondrial proteins involved in fatty acid transport and fatty acid oxidation, including the alpha and beta subunits of the trifunctional protein, fatty acid AcylCoA synthase, Fatty AcylCoA dehydrogenases, and Carnitine palmitoyl transferase 2. Notably, comparisons of the structures of GLP-1(28-36)amide with those of hexarelin and pentagastrin show striking similarities (see Table 4).

TABLE 4

Hydrophobic, amphipathic alpha helices in C-terminal regions of peptide hormones that mimic the structure of short chain fatty acids and are predicted to bind to and be transported by the CD36 fatty acid translocase

| Peptide | Sequence | Seq ID No. |
|---|---|---|
| Hexarelin | H-W(Me)-A-W-F-Kamide | 16 |
| GLP-1 | F-I-A-W-L-V | 17 |
| Exd4 | F-I-E-W-L-K | 18 |
| GIP (3-31) | F-V-N-W-L-L | 19 |
| Glucagon | F-V-Q-W-L-M | 20 |
| Gastrin-C | A-Y-G-W-M-D-Famide | 21 |
| GHRP6 | H-W-K-W-F-Kamide | 22 |
| CCK8 | Y-M-G-W-M-D-Famide | 23 |
| Ghrelin (3) | S-M-L-W-M-D | 24 |
|  | L-E-G-W-L-H | 25 |
|  | D-I-L-W-E-V | 26 |

The sequences in Table 4 were aligned based on the known conservation of Tryptophan residues in proteins. These are hydrophobic, small helical amphipathic sequences and could mimic a fatty acid chain.

In all of these C-terminal hormone peptide sequences the amino acid tryptophan (W) is highly conserved. Tryptophan residues in proteins are known to be amongst the most highly conserved of all of the amino acids in the evolution of protein sequences (Dayhoff et al., Methods Enzymol 91:524-545, 1983). Furthermore, the secondary structures of these C-terminal peptide sequences shown in Table 2 all model as amphipathic alpha helices. It is envisioned that these regions of sequence in the peptide hormones would be strongly favored to assume a helical conformation in the hydrophobic environment of fatty acids when present in a fatty acid transport pathway.

This is of interest because hexarelin is reported to promote mitochondrial biogenesis and a fat burning phenotype (Rodrigue-Way et al., Endocrinology. 148(3):1009-18 (2007)) in white adipocytes and gastrin is shown to enter cells and interact with (inhibit) the alpha subunit of the trifunctional protein (HADHA) involved in beta oxidation (Hashimoto et al., J Biochem. 119(6):1196-201 (1996)).

The findings described herein indicate that the cleavage of GLP-1 by NEP24.11 does not degrade GLP-1 but rather generates a new novel bioactivity involved in the regulation of fat metabolism and energy balance. These findings also may have potential implications for the pathogenesis and treatment of obesity, metabolic syndrome.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating metabolic syndrome in a subject, the method comprising administering to the subject a therapeutically effective amount of a peptide consisting of the amino acid sequence of (Phe/Tyr)-Ile-Ala-Trp-Leu-Val-(Lys/Arg)-Gly-Arg-Xaa (SEQ ID NO:1), wherein Xaa is Gly-Arg or Gly-Arg-Gly, wherein one or more amino acids of the peptide are alkylated, acylated, or biotinylated.

2. The method of claim 1, wherein the peptide is amidated.

3. A method of treating obesity in a subject, the method comprising administering to the subject a therapeutically effective amount of a peptide consisting of the amino acid sequence of (Phe/Tyr)-Ile-Ala-Trp-Leu-Val-(Lys/Arg)-Gly-Arg-Xaa (SEQ ID NO:1), wherein Xaa is Gly-Arg or Gly-Arg-Gly, wherein one or more amino acids of the peptide are alkylated, acylated, or biotinylated.

4. The method of claim 3, wherein the peptide is amidated.

5. A method of treating metabolic syndrome in a subject, the method comprising administering to the subject a therapeutically effective amount of a fusion peptide comprising a first portion consisting of the amino acid sequence of (Phe/Tyr)-Ile-Ala-Trp-Leu-Val-(Lys/Arg)-Gly-Arg-Xaa (SEQ ID NO:1), wherein Xaa is Gly-Arg or Gly-Arg-Gly, fused to a cell-penetrating peptide, wherein one or more amino acids of the fusion peptide are alkylated, acylated, or biotinylated.

6. The method of claim 5, wherein the cell-penetrating peptide is fused to the C-terminus of the first portion.

7. The method of claim 5, wherein the cell-penetrating peptide is selected from the group consisting of HIV-derived TAT peptides, penetratins, transportans, SS peptides, and hCT derived cell-penetrating peptides.

8. A method of treating obesity in a subject, the method comprising administering to the subject a therapeutically effective amount of a fusion peptide comprising a first portion consisting of the amino acid sequence of (Phe/Tyr)-Ile-Ala-Trp-Leu-Val-(Lys/Arg)-Gly-Arg-Xaa (SEQ ID NO:1), wherein Xaa is Gly-Arg or Gly-Arg-Gly, fused to a cell-penetrating peptide, wherein one or more amino acids of the fusion peptide are alkylated, acylated, or biotinylated.

9. The method of claim 8, wherein the cell-penetrating peptide is fused to the C-terminus of the first portion.

10. The method of claim 8, wherein the cell-penetrating peptide is selected from the group consisting of HIV-derived TAT peptides, penetratins, transportans, SS peptides, and hCT derived cell-penetrating peptides.

11. The method of claim 1, wherein Xaa is Gly-Arg.

12. The method of claim 3, wherein Xaa is Gly-Arg.

13. The method of claim 5, wherein Xaa is Gly-Arg.

14. The method of claim 8, wherein Xaa is Gly-Arg.

15. The method of claim 1, wherein Xaa is Gly-Arg-Gly.

16. The method of claim 3, wherein Xaa is Gly-Arg-Gly.

17. The method of claim 5, wherein Xaa is Gly-Arg-Gly.

18. The method of claim 8, wherein Xaa is Gly-Arg-Gly.

* * * * *